(12) United States Patent
Inari et al.

(10) Patent No.: US 8,247,605 B2
(45) Date of Patent: *Aug. 21, 2012

(54) METHOD OF REPLACING DISPERSION MEDIUM

(75) Inventors: Masato Inari, Okayama (JP); Fumiya Zaima, Okayama (JP)

(73) Assignees: Mitsubishi Gas Chemical Company, Inc., Tokyo (JP); Toyobo Co., Ltd., Osaka (JP); Mizushima Aroma Company, Ltd., Okayama (JP)

(*) Notice: Subject to any disclaimer, the term of this patent is extended or adjusted under 35 U.S.C. 154(b) by 636 days.

This patent is subject to a terminal disclaimer.

(21) Appl. No.: 12/374,835

(22) PCT Filed: Jul. 19, 2007

(86) PCT No.: PCT/JP2007/064286
§ 371 (c)(1),
(2), (4) Date: Jan. 23, 2009

(87) PCT Pub. No.: WO2008/013100
PCT Pub. Date: Jan. 31, 2008

(65) Prior Publication Data
US 2010/0004484 A1    Jan. 7, 2010

(30) Foreign Application Priority Data

Jul. 24, 2006 (JP) ................................. 2006-200909

(51) Int. Cl.
*C07C 51/42* (2006.01)
(52) U.S. Cl. ..................................................... 562/485
(58) Field of Classification Search .................. None
See application file for complete search history.

(56) References Cited

U.S. PATENT DOCUMENTS
2,794,832 A    6/1957   Rietema
(Continued)

FOREIGN PATENT DOCUMENTS
DE    31 28 474    6/1982
(Continued)

OTHER PUBLICATIONS

Extended European Search Report, including European Search Opinion and Supplementary European Search Report, dated Oct. 11, 2010, for EP Application No. 07791039.6-2103/2050732 (PCT/JP2007/064286).

(Continued)

*Primary Examiner* — Jafar Parsa
*Assistant Examiner* — Jennifer C Sawyer
(74) *Attorney, Agent, or Firm* — Antonelli, Terry, Stout & Kraus, LLP.

(57) ABSTRACT

A method of replacing a first dispersion medium in a starting slurry composed of the first dispersion medium and isophthalic acid crystals with a second dispersion medium. The starting slurry is tangentially fed to a vertically extending cylindrical portion of a cyclone-shaped nozzle disposed at an upper portion of a replacement tank of a dispersion medium replacement apparatus, from a tangential direction of the cylindrical portion. The fed starting slurry moves circularly along an inner wall of the cylindrical portion. The slurry circularly moving is then discharged from an opening which is disposed at a vertically lower end of the cylindrical portion and dispersed in a second dispersion medium which is fed from a lower portion of the replacement tank. The replaced slurry composed of isophthalic acid crystals and the second dispersion medium is mainly discharged from the lower portion of the replacement tank, and the first dispersion medium is mainly withdrawn from the upper portion of the replacement tank.

8 Claims, 5 Drawing Sheets

U.S. PATENT DOCUMENTS

| | | | |
|---|---|---|---|
| 3,534,090 A * | 10/1970 | Bryant et al. | 562/414 |
| 3,839,436 A * | 10/1974 | Longland | 562/414 |
| 3,917,681 A | 11/1975 | Shinn et al. | |
| 4,212,995 A * | 7/1980 | Shiraki | 562/485 |
| 5,712,412 A | 1/1998 | Inary et al. | |

FOREIGN PATENT DOCUMENTS

| | | |
|---|---|---|
| EP | 0 822 176 A2 | 2/1998 |
| JP | 57-053431 | 3/1982 |
| JP | 07-002732 | 1/1995 |
| JP | 07-274963 | 10/1995 |
| JP | 08-308309 | 11/1996 |
| JP | 2001-247868 | 9/2001 |
| JP | 3269508 | 1/2002 |

OTHER PUBLICATIONS

EP Official Action dated Apr. 26, 2012, for EP Application No. 07 791 039.6-2103.

* cited by examiner

METHOD OF REPLACING DISPERSION MEDIUM

TECHNICAL FIELD

The present invention relates to a method of replacing a first dispersion medium in a starting slurry composed of the first dispersion medium and a isophthalic acid crystal with a second dispersion medium. More specifically, the present invention relates to an efficient method of replacing a first dispersion medium in a starting slurry composed of the first dispersion medium and isophthalic acid crystals, which is produced by a liquid-phase oxidation reaction or obtained by a treatment of crude isophthalic acid by a catalytic hydrogenation or recrystallization and which contains a large amount of impurities, with a second dispersion medium. The method of the present invention is suitably used for producing a high-purity isophthalic acid.

BACKGROUND ART

Isophthalic acid is produced by a liquid-phase oxidation reaction of m-dialkylbenzenes such as m-xylene. In general, the m-dialkylbenzene is subjected to a liquid-phase oxidation reaction in acetic acid solvent in the presence of a catalyst such as cobalt and manganese or in the co-presence of the catalyst and an accelerator such as a bromine compound and acetaldehyde to obtain a crude isophthalic acid, and then the resultant crude isophthalic acid is purified to obtain the aimed high-purity isophthalic acid.

However, since acetic acid is used as a solvent in the above reaction and the reaction product contains impurities such as 3-carboxybenzaldehyde (3CBA) and m-toluic acid (m-TOL), a high purification technique is required to obtain the high-purity isophthalic acid.

There are known various methods for purifying the crude isophthalic acid obtained by the above reaction, such as a method of dissolving the crude isophthalic acid in acetic acid, water or an acetic acid/water mixed solvent under high-temperature and high-pressure and then subjecting the resultant solution to catalytic hydrogenation, decarbonylation, oxidation or recrystallization, and a method of subjecting a dispersion partially dissolving isophthalic acid crystal to high-temperature immersion treatment.

In both the production of the crude isophthalic acid by the liquid-phase oxidation reaction and the purification thereof, the separation of the isophthalic acid crystal from the resultant slurry is finally needed. When the dispersion medium (first dispersion medium) of the reaction product solution obtained by the liquid-phase oxidation reaction is acetic acid and a different dispersion medium (second dispersion medium) such as water is used in the purification, it is required to first separate the crystals from the reaction product solution and then re-disperse the separated crystals in the second dispersion medium. When the first dispersion medium in the reaction product solution is the same kind as the second dispersion medium for the subsequent purification, a substantial part of the impurities such as oxidation intermediate, for example, 3CBA and m-TOL and coloring substances remain dissolved in the dispersion medium after a high-temperature purifying operation of the reaction product solution of the liquid-phase oxidation reaction or the starting slurry composed of the first dispersion medium and isophthalic acid crystals. If the reaction product solution of the liquid-phase oxidation reaction or the starting slurry composed of the first dispersion medium and isophthalic acid crystals is cooled to about 100° C. while allowing the impurities to be dissolved therein, the impurities are included into the isophthalic acid crystals, thereby failing to obtain the aimed high-purity isophthalic acid. Therefore, it is necessary to conduct the separation at high temperatures under high pressures to separate a high-purity isophthalic acid from the reaction product solution obtained by the liquid-phase oxidation reaction, the starting slurry composed of the first dispersion medium and isophthalic acid crystals or the slurry after the purification treatment.

A centrifugal separation has been most generally used for separating a slurry into crystals and a dispersion medium, which is also extensively used in the separation of the reaction product solution obtained by the liquid-phase oxidation reaction or the starting slurry composed of the first dispersion medium and isophthalic acid crystals.

In the centrifugal separation, the starting slurry composed of the first dispersion medium and isophthalic acid crystals is introduced into a basket which is rotating at a high speed to allow the first dispersion medium to overflow from the upper portion of the basket and allow the crystals to move downwardly. It has been known that this method involves several problems caused by the limitation in the structures and functions due to the operation at high temperatures under high pressures.

Since the rinsing during the centrifugal separation and the rinsing of the separated crystals are difficult in this method, the amount of the first dispersion medium adhering to the crystals increases. Therefore, the centrifugally separated isophthalic acid crystals are made into a slurry by a further addition of a high-temperature fresh solvent, thereby needing an additional separation into the crystals and the dispersion medium. In addition, the high-speed rotation at high temperatures under high pressures necessitates a difficult and complicated maintenance of the centrifugal separator, to increase the production costs.

For example, in the method for producing a high-purity isophthalic acid disclosed in Patent Document 1, a crude isophthalic acid obtained by a liquid-phase oxidation is catalytically hydrogenated and isophthalic acid is allowed to crystallize to obtain a slurry which is then brought into contact with a hot water to exchange the dispersion medium. It is reported that the quality of isophthalic acid which is taken out of the bottom of a tower for replacing dispersion medium is increased by discharging a part of fine isophthalic acid crystals together with the mother liquor of slurry from the top of tower. However, Patent Document 1 is completely silent about the uniform dispersion of the isophthalic acid crystals in the tower for replacing dispersion medium.

[Patent Document 1] Japanese Patent 3269508

DISCLOSURE OF THE INVENTION

An object of the present invention is to provide a method of replacing a dispersion medium with another which is capable of uniformly dispersing isophthalic acid crystals contained in a starting slurry composed of the isophthalic acid crystals and a first dispersion medium in the horizontal direction of an apparatus, and further stably operating the replacing operation for a long period of time.

The inventors have tried to replace the dispersion medium by bringing a slurry containing isophthalic acid crystals into contact with a hot water using a known distributor which regulates the flow by throttling respective injection orifices. However, this method failed to disperse the isophthalic acid crystals uniformly in the horizontal direction and did not allow a stable operation for a long period of time. As a result of extensive study for solving these problems, the inventors have come to the use of a centrifugal force to enhance the uniform dispersion of the crystals and found a method of replacing a dispersion medium with another using a cyclone-shaped nozzle having a simple structure and a good dispersion efficiency.

Thus, the present invention relates to a method of replacing a dispersion medium with another, comprising the steps of:

feeding a starting slurry composed of a first dispersion medium and isophthalic acid crystals to a cyclone-shaped nozzle disposed at an upper portion of a replacement tank of a dispersion medium replacement apparatus;

contacting the starting slurry discharged from the cyclone-shaped nozzles with a second dispersion medium which is fed from a lower portion of the replacement tank and flows upwardly through the replacement tank; and mainly discharging a replaced slurry composed of isophthalic acid crystal and the second dispersion medium from the lower portion of the replacement tank and mainly withdrawing the first dispersion medium from the upper portion of the replacement tank, the cyclone-shaped nozzle being composed of a cylindrical portion having a vertically extending axis and an opening disposed at a vertically lower end, the starting slurry being tangentially fed to the cylindrical portion so as to allow the starting slurry to move circularly along an inner wall of the cylindrical portion, and the starting slurry which moves circularly being discharged from the opening, thereby dispersing the starting slurry in the second dispersion medium.

BRIEF DESCRIPTION OF THE DRAWINGS

FIG. 1*a* is a perspective view showing an example of a cyclone-shaped nozzle, and FIG. 1*b* is a sectional view taken along the line V-V in FIG. 1*a*.

FIG. 2*a* is a perspective view showing another example of a cyclone-shaped nozzle, and FIG. 2*b* is a sectional view taken along the line V-V in FIG. 2*a*.

FIG. 3*a* is a perspective view showing still another example of a cyclone-shaped nozzle, and FIG. 3*b* is a sectional view taken along the line V-V in FIG. 3*a*.

FIG. 4 is a schematic view showing a manner of tangentially distributively feeding a starting slurry from a ring header into inlets of cyclone-shaped nozzles.

FIG. 5 is a schematic view showing an example of a dispersion medium replacement apparatus.

FIG. 6 is a perspective view showing a cyclone-shaped nozzle.

FIG. 7 is a graph showing the distribution of slurry concentration in a tank in Reference Example 1.

FIG. 8 is a graph showing the distribution of slurry concentration in a tank in Comparative Example 1.

FIG. 9 is a schematic view showing another example of a dispersion medium replacement apparatus.

FIG. 10 is a graph showing the distribution of slurry concentration in a tank in Example 1.

FIG. 11 is a schematic cross-sectional view of cyclone-shaped nozzle for showing the shape of weir.

BEST MODE FOR CARRYING OUT THE INVENTION

The dispersion medium replacement apparatus used in the present invention includes a cyclone-shaped nozzle. Examples of the cyclone-shaped nozzle are shown in FIGS. 1 to 3. However, the structure, shape, etc., of the cyclone-shaped nozzle are not particularly limited to those shown in these figures as long as it satisfies the following conditions.

The cyclone-shaped nozzle has a feed portion 21 for feeding a starting slurry and a cylindrical portion (hollow body of revolution) 20 connected to the feed portion. The cylindrical portion has a vertically extending axis (i.e., the cylindrical portion extends in the vertical direction). Opening 28, 29 is disposed at vertically upper and lower ends, at least at vertically lower end of the cylindrical portion. The feed portion 21 is disposed so as to allow the starting slurry to be tangentially fed to the cylindrical portion 20. The starting slurry is fed to the cylindrical portion 20 so as to move circularly along an inner wall of the cylindrical portion. The starting slurry which moves circularly is forced to move toward the inner wall of the cylindrical portion by the action of a centrifugal force and the vicinity of the inner wall is filled with the starting slurry which is circularly moving. The starting slurry flows downwardly while moving circularly, and then discharged from the opening 29 of the cylindrical portion 20, which is formed at the vertically lower end, while keeping the circular motion. The starting slurry discharged from the cylindrical portion 20 is widely distributed and dispersed in the horizontal direction by the action of the centrifugal force. Since the diameter of the opening 29 can be made sufficiently large as compared to the diameter of pores of the conventional distributor, the clogging of the opening does not occur even after operating for a long period of time. Weir 22, 34 is preferably formed at the lower portion of the cylindrical portion 20, and, if necessary, at its upper portion.

As described above, it is important for the cyclone-shaped nozzle used in the present invention to satisfy the following basic structures (1) to (3):

(1) Including a feed portion for feeding the starting slurry and a cylindrical portion having a vertically extending axis which is connected to the feed portion such that the starting slurry is tangentially fed to the cylindrical portion.

(2) An opening for discharging the starting slurry which is circularly moving is provided at the vertically lower end of the cylindrical portion. Another opening is optionally provided at the vertically upper end of the cylindrical portion.

(3) A weir is provided at the lower portion of the cylindrical portion and at its upper portion, if necessary.

The cylindrical portion (hollow body of revolution) having a vertically extending axis allows the starting slurry fed thereto to move circularly along the inner wall of the cylindrical portion. In the present invention, it is important to feed the starting slurry from the nozzle into the dispersion medium replacement apparatus while keeping the circular motion of the starting slurry, thereby uniformly distributing and dispersing the starting slurry in the horizontal direction by the action of the centrifugal force. Therefore, the structure of cylindrical portion is not particularly limited unless the circular motion of the starting slurry is inhibited. In order to allow the fed starting slurry to move circularly along the inner wall of the cylindrical portion, the feed portion and the cylindrical portion are preferably connected to each other so as to tangentially feed the starting slurry to the cylindrical portion.

The opening for allowing the starting slurry which is circularly moving to enter into the dispersion medium replacement apparatus is provided at a vertically lower end of the cyclone-shaped nozzle, as shown in FIGS. 1 to 3. In case of preventing the starting slurry from being dispersed or scattered from the upper end of the cylindrical portion, no opening is formed on the upper end (FIG. 3).

To allow the starting slurry to maintain the circular motion, a lower weir 23 is preferably provided as shown in FIGS. 1 to 3. An upper weir 22 may be disposed, if necessary. The weir is formed so as to extend from the inner wall of the cylindrical portion 20 toward the center of the cylindrical portion horizontally or with a vertically downward slant. With such a weir, the starting slurry fed is prevented from being immediately discharged from the cyclone-shaped nozzle into the dispersion medium replacement apparatus. The shape of the upper weir 22 and lower weir 23 is schematically shown in FIGS. 11a to 11g with a cross-sectional view of the cyclone-shaped nozzle.

In the method of replacing a dispersion medium with another according to the present invention, the starting slurry composed of the first dispersion medium and isophthalic acid crystals is fed to the cyclone-shaped nozzle disposed at an upper portion of the dispersion medium replacement apparatus. The second dispersion medium is fed from a lower portion of the dispersion medium replacement apparatus. From the lower portion of the dispersion medium replacement apparatus, the resultant replaced slurry composed of isophthalic acid crystals and the second dispersion medium is mainly discharged, and the first dispersion medium is mainly discharged from the upper portion.

As the starting slurry containing the first dispersion medium and isophthalic acid crystals, usable are a reaction product solution of the liquid-phase oxidation and a slurry obtained in the recrystallization of crude isophthalic acid.

The reaction product solution of the liquid-phase oxidation is obtained in the liquid-phase oxidation of m-dialkylbenzene such as m-xylene in an acetic acid solvent in the presence of a catalyst such as cobalt and manganese or in the co-presence of the catalyst and an accelerator such as bromine compounds and acetaldehyde. The first dispersion medium of the reaction product solution of the liquid-phase oxidation is the mother liquor of the oxidation reaction mainly composed of acetic acid. The concentration of isophthalic acid in such starting slurry is preferably from 10 to 45% by weight, and the concentration of acetic acid in the first dispersion medium is preferably from 70 to 100% by weight. The temperature of the starting slurry to be fed to the dispersion medium replacement apparatus is preferably from 80 to 220° C.

In the purification of the reaction product solution of the liquid-phase oxidation (starting slurry), either of acetic acid optionally containing water or water is used as the second dispersion medium. The concentration of water in the second dispersion medium is preferably from 50 to 100% by weight. Also, when isophthalic acid crystals are re-dispersed in water, the second dispersion medium is water.

The recrystallization slurry of crude isophthalic acid is obtained in the step where crude isophthalic acid is dissolved in acetic acid, water or a mixed solvent thereof at a high temperature under a high pressure and then subjected to a catalytic hydrogenation, decarbonylation, oxidation, or recrystallization. The first dispersion medium in the recrystallization slurry of crude isophthalic acid is acetic acid or water which dissolves impurities during the recrystallization, and the second dispersion medium is water. The concentration of isophthalic acid in the recrystallization slurry is preferably from 10 to 45% by weight. The temperature of the recrystallization slurry to be fed to the dispersion medium replacement apparatus is preferably from 60 to 180° C.

The opening area of the outlet for discharging the starting slurry from the cyclone-shaped nozzle, i.e., the area of the opening disposed at the lower end of the cylindrical portion is preferably from 0.03 to 0.8 $m^2$. The number of the cyclone-shaped nozzles per horizontal sectional area of the dispersion medium replacement apparatus is preferably from 0.3 to $2/m^2$. The number of the cyclone-shaped nozzles is determined depending upon the size of the dispersion medium replacement apparatus and the region (dispersing area) through which the starting slurry discharged from the cyclone-shaped nozzles is horizontally dispersed. The effective dispersing area of one cyclone-shape nozzle is generally 3 $m^2$ or less. Therefore, the number of the cyclone-shaped nozzles per a unit sectional area of the dispersion medium replacement apparatus is required to be $0.3/m^2$ or more. The number of the cyclone-shaped nozzles per unit sectional area may be made as large as possible. However, if the number of the cyclone-shaped nozzles is excessively large, the uniform feed of the starting slurry to respective cyclone-shaped nozzles becomes difficult. Therefore, in view of the size of the apparatus industrially used and the performance of the cyclone-shaped nozzles, the number of the cyclone-shaped nozzles exceeding $2/m^2$ is disadvantageous for the industrial production.

The feed of the starting slurry to two or more cyclone-shaped nozzles is made by various methods. The most suitable method for the uniform feeding is to control the flow rate for each cyclone-shaped nozzle, but this method is costly.

In another method, the concentrated feeding of the starting slurry to some cyclone-shaped nozzle is prevented by controlling the flow rate by orifices or valves on the basis of the pressure difference between each pair of cyclone-shaped nozzles which is technically calculated according to the design of the cyclone-shaped nozzle. This method may be sufficient in a certain size of apparatus. Taking the complexity of the slurry as a fluid and the accuracy of the technical calculation into account, it is difficult to uniformly feed the starting slurry to a large-scaled apparatus, i.e., a large number of the cyclone-shaped nozzles.

In such a large-scaled apparatus having a large number of the cyclone-shaped nozzles, the starting slurry can be fed quite uniformly into the cyclone-shaped nozzles by the device as shown in FIG. 4 which has a very simple structure, wherein two or more cyclone-shaped nozzles are connected to a ring header and the starting slurry fed to the ring header is distributed to respective cyclone-shaped nozzles. The starting slurry is preferably fed to respective cyclone-shaped nozzles along a tangential direction of the ring header. If being fed in this manner, the starting slurry is fed to respective cyclone-shaped nozzles while keeping the circular motion in the ring header. The starting slurry fed to respective cyclone-shaped nozzles is then discharged into the dispersion medium replacement apparatus while keeping the circular motion, and distributed and dispersed while moving circularly. With such a fractal structure of vortex flows, the first dispersion medium in the starting slurry is effectively replaced with the second dispersion medium. By the use of the ring header, the starting slurry is uniformly fed to respective cyclone-shaped nozzles even when the flow rate of the starting slurry fed to the ring header varies. This effect cannot be achieved by the method of regulating the flow rate by orifices or valves.

An example of the dispersion medium replacement apparatus is shown in FIG. 9. The starting slurry (isophthalic acid crystals/first dispersion medium) is fed to a cyclone-shaped nozzle 16 disposed at an upper portion of a replacement tank 12 made of stainless steel, etc. through a feed valve 14 and a feed port 15. In the industrial operation, the replacement tank 12 preferably has a diameter of from 0.3 to 7 m and a height of from 1 to 20 m. The diameter of the a cylindrical portion of the cyclone-shaped nozzle 16 is preferably from 0.1 to 1 m. The feeding speed of the starting slurry to be fed to the cyclone-shaped nozzle 16 is not particularly limited as long as the starting slurry is discharged from the cyclone-shaped nozzle 16 while keeping the circular motion. When the replacement tank 12 and the cyclone-shaped nozzle 16 have the sizes mentioned above, the feeding speed is preferably from 0.5 to 50 t/h.

The second dispersion medium is fed from a feed port 18 disposed in the vicinity of a bottom of the replacement tank 12 through a valve preferably at a feeding speed of from 0.3 to 40 t/h. The second dispersion medium fed flows upwardly in the replacement tank 12. The starting slurry discharged from the cyclone-shaped nozzle 16 is brought into contact with the upward flow of the second dispersion medium, and uniformly distributed and dispersed into the second dispersion medium in a horizontal direction while keeping the circular motion. The dispersed isophthalic acid crystals gravitationally sediment throughout the phase rich in the second dispersion medium, and the replaced slurry composed of isophthalic acid crystals and mainly the second dispersion medium is concentrated in the lower portion of the replacement tank 12. The replaced slurry is discharged from an outlet port 19 using a discharge pump 13. The inner temperature of the replacement tank 12 is preferably kept at from 80 to 180° C.

The first dispersion medium is forced upwardly by the ascending second dispersion medium and discharged outside of the apparatus from a discharge port 20.

EXAMPLES

The present invention is described in more detail below by referring to the following examples. However, these examples are only illustrative and not intended to limit the invention thereto.

Reference Example 1

Figure 1A:
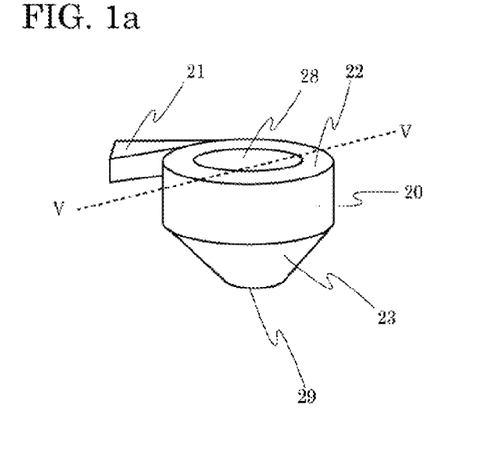
Figure 1B:
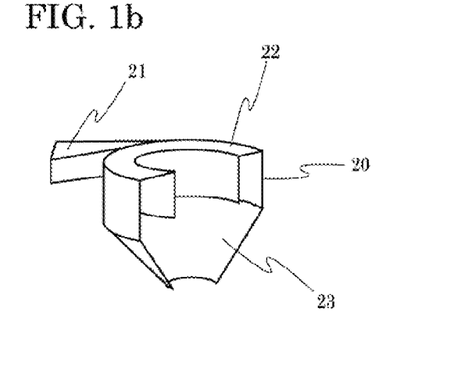
Figure 2A:
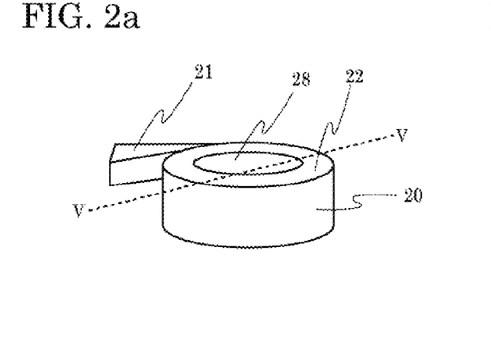
Figure 2B:
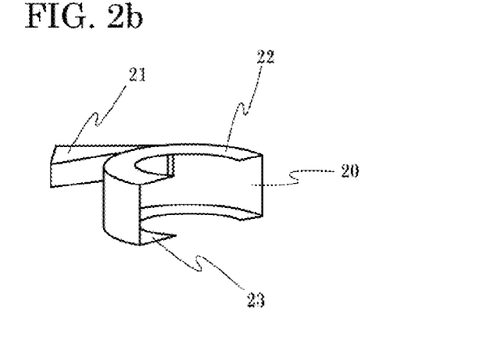
Figure 3A:
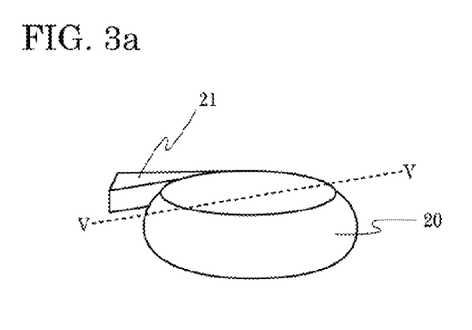
Figure 3B:
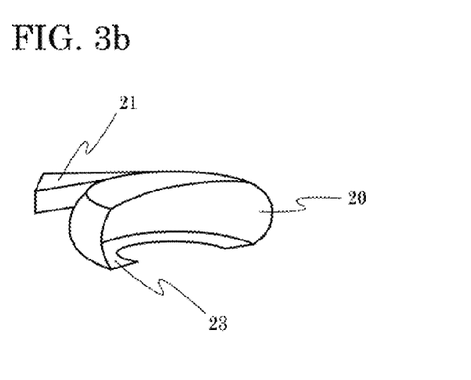
Figure 4:
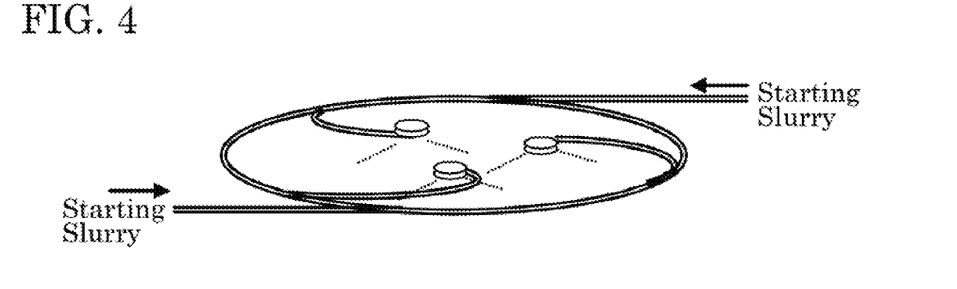
Figure 5:
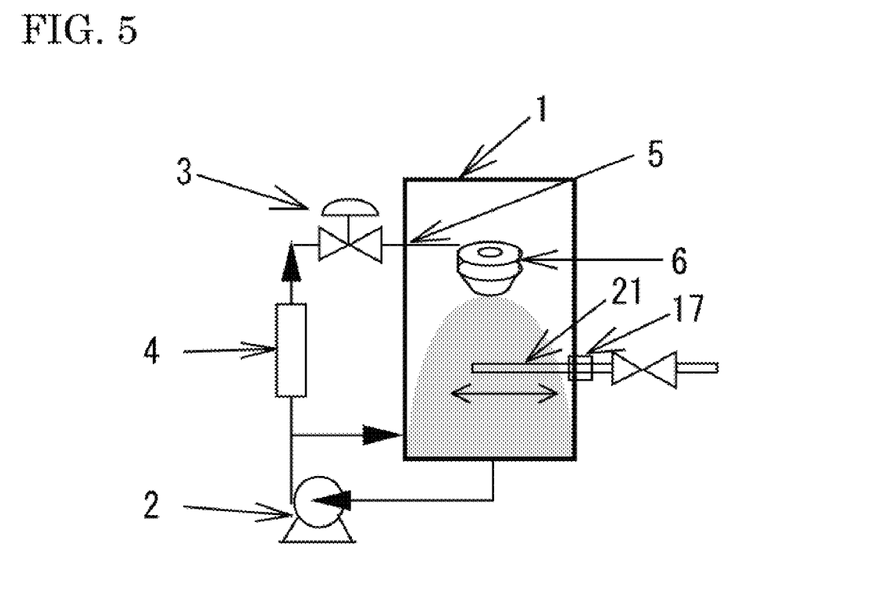

Using an experimental apparatus as shown in FIG. 5, the state of dispersion in an experimental replacement tank 1 (diameter: 2 m and height: 4 m) was observed. A water slurry of sand having a regulated particle size (average particle size: 95 μm; concentration of sand: 35% by weight) was used as a starting slurry. The starting slurry was charged into the experimental replacement tank 1 and circulated to a feed port 5 through an electromagnetic flow meter 4 and a flow control valve 3 by using a circulation pump 2 while preventing the sand from being deposited on the bottom of the tank.

Figure 6:
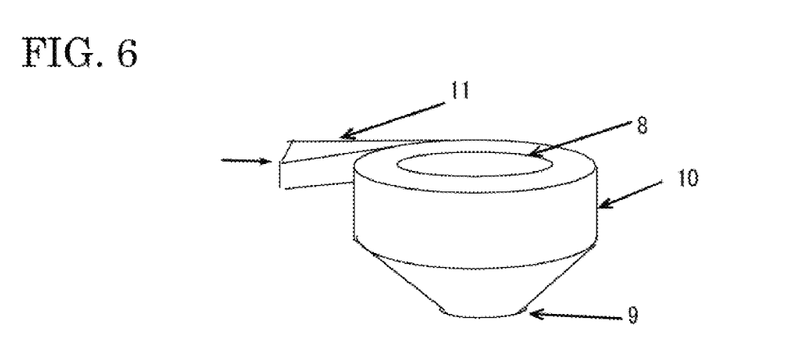

The circulated starting slurry was fed to the cyclone-shaped nozzle 6, and then discharged and dispersed into the experimental replacement tank 1 while keeping the circular motion. The structure of the cyclone-shaped nozzle 6 is shown in FIG. 6. A feed portion 11 for feeding the starting slurry was connected to a cylindrical portion 10 so as to tangentially feed the starting slurry. On the vertically upper and lower ends of the cylindrical portion 10 (inner diameter: 0.70 m), an opening 8 (opening diameter: 0.58 m) and an opening 9 (opening diameter: 0.43 m) were provided, respectively.

Figure 7:
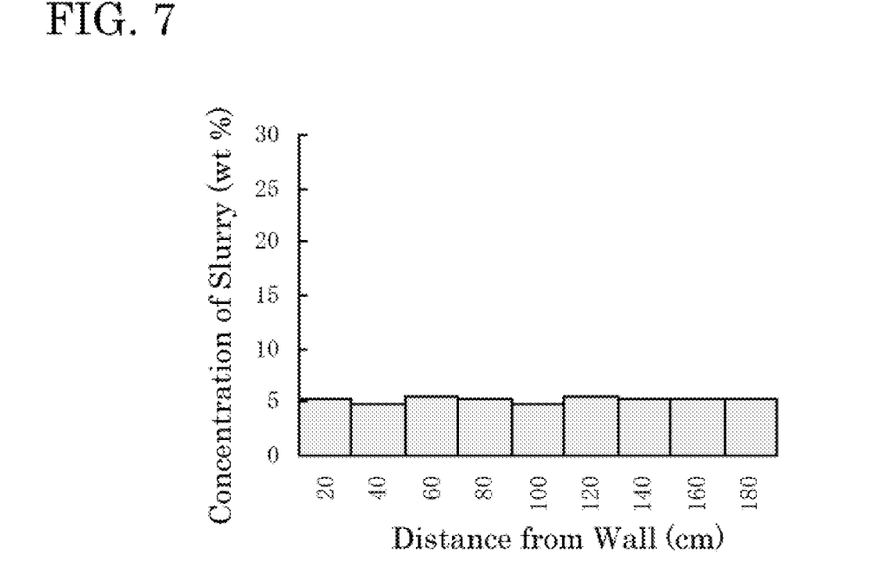

The slurry was sampled through a sampling nozzle 21 (disposed at a height of 1.50 m from the bottom of the experimental replacement tank 1) which was disposed through a sampling opening 17 so as to radially move within the experimental replacement tank 1, and the concentration of slurry (concentration of sand in the slurry) was measured. The results are shown in the graph of FIG. 7. As seen from FIG. 7, the sand was uniformly dispersed in the horizontal direction.

The slurry was continuously circulated for 6 h, during which no clogging of the cyclone-shaped nozzle occurred.

Comparative Example 1

Figure 8:
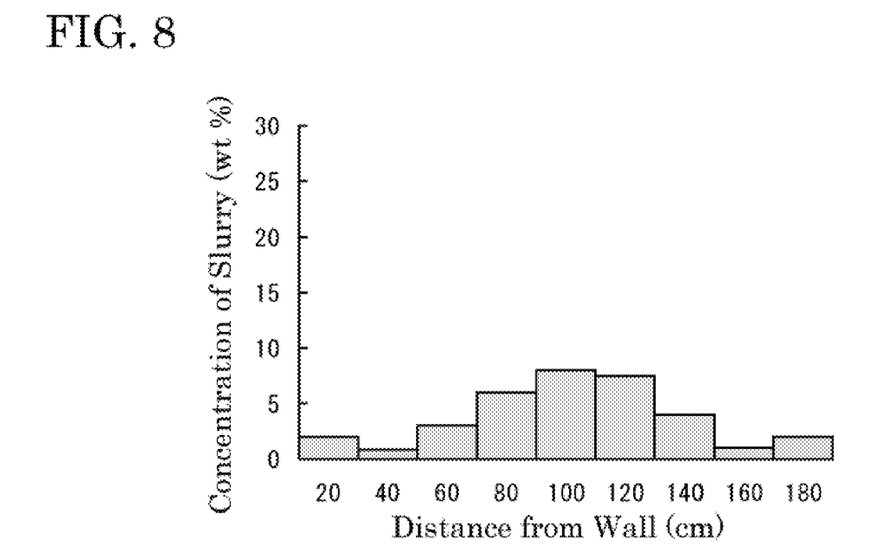

The same procedure as in Reference Example 1 was repeated except for using a feed nozzle made of an L-shaped tube having a downward opening in place of the cyclone-shaped nozzle, to measure the slurry concentration distribution within the experimental replacement tank 1. The results are shown in FIG. 8. As seen FIG. 8, the sand was not uniformly dispersed in the horizontal direction.

Comparative Example 2

The starting slurry was circulated in the same manner as in Comparative Example 1 except for attaching a pigtail disperser to the L-shaped feed nozzle used in Comparative Example 1. After 10 min from starting the circulation, the feed nozzle was clogged.

Example 1

Figure 9:
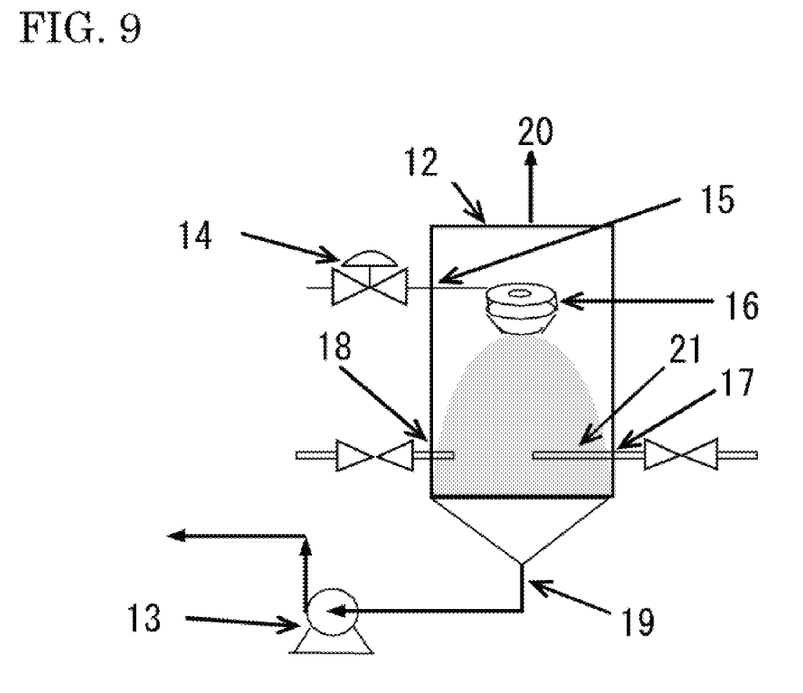

Using an apparatus having the same structure as shown in FIG. 9, the replacement of the dispersion medium to another was conducted. As the replacement tank, a closed container made of stainless steel having an inner diameter of 30 cm and a height of 100 cm was used.

The closed container was filled with water maintained at 100° C. A starting slurry composed of 30% by weight of isophthalic acid and water as a first dispersion medium was fed at a rate of 770 kg/h to the same cyclone-shaped nozzle as used in Example 1. Water as a second dispersion medium was fed at a rate of 560 kg/h from a lower portion of the replacement tank. From the lower portion of the replacement tank, the replaced slurry composed of isophthalic acid crystals and the second dispersion medium was mainly discharged. From the upper portion of the replacement tank, the first dispersion medium was mainly withdrawn. The replacement of the dispersion medium to another was continuously performed for one week, during which no troubles such as clogging occurred.

Figure 10:
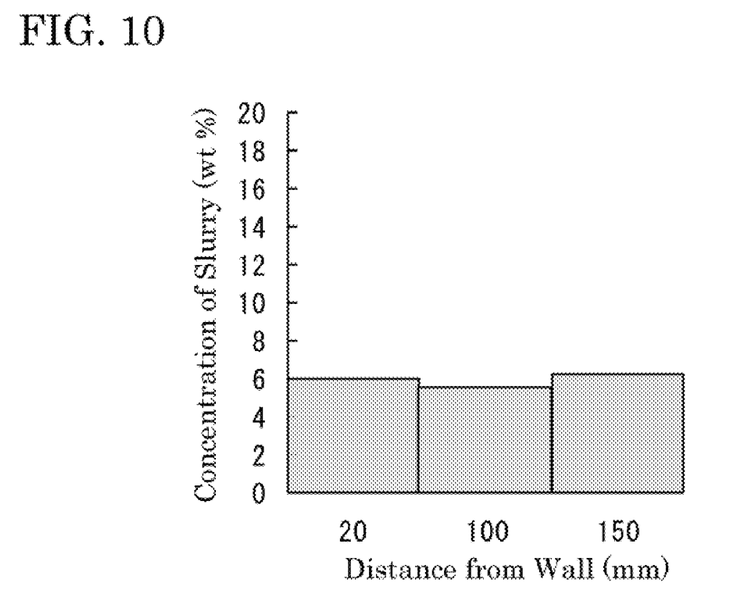
Figure 11A:
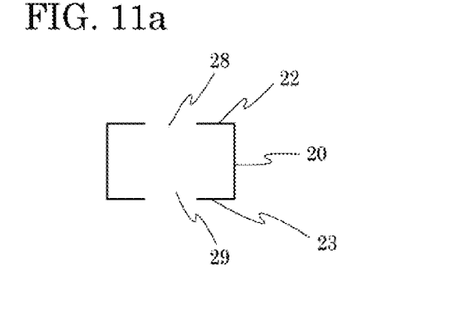
Figure 11B:
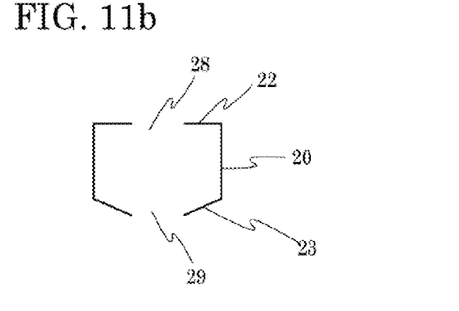
Figure 11C:
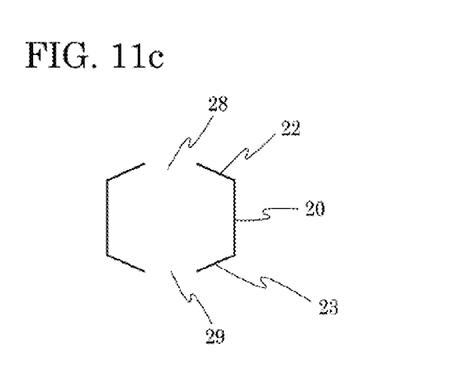
Figure 11D:
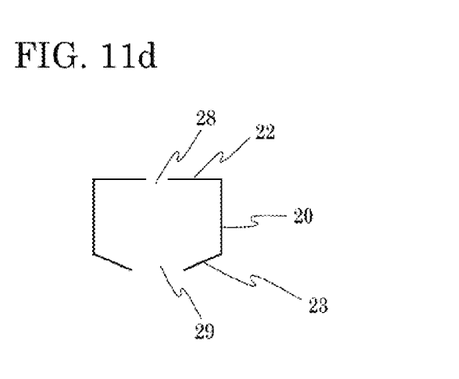
Figure 11E:
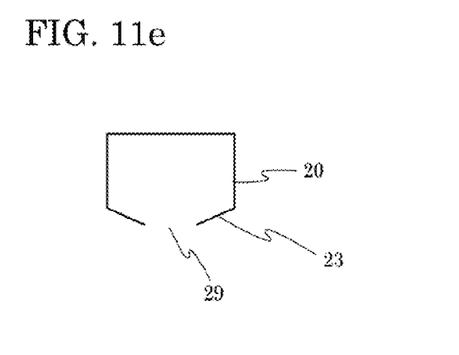
Figure 11F:
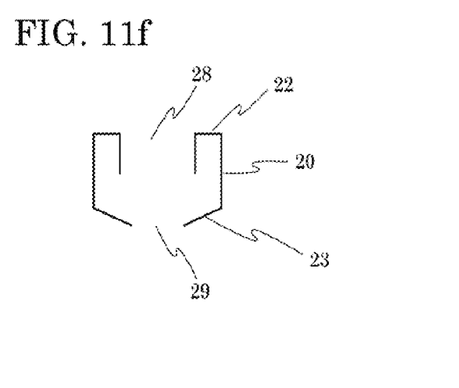
Figure 11G:
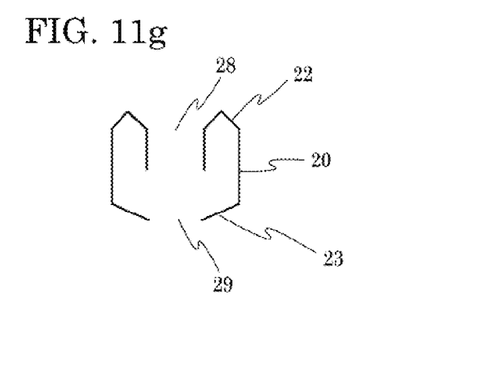

The slurry in the replacement tank was sampled using a sampling nozzle 21 which was disposed through a sampling opening 17 at horizontally different positions (at a height of 40 m from the bottom of the replacement tank), to measure the concentration of the slurry (concentration of isophthalic acid crystals in the slurry). As shown in the graph of FIG. 10, isophthalic acid crystals were uniformly dispersed in the horizontal direction.

INDUSTRIAL APPLICABILITY

In the method of replacing a dispersion medium with another according to the present invention, a cyclone-shaped nozzle satisfying the specific requirements is used. By feeding a starting slurry composed of a first dispersion medium and isophthalic acid crystals through such a cyclone-shaped nozzle, isophthalic acid crystals are uniformly dispersed in the horizontal direction, and the replacement operation is stably conducted for a long period of time.

What is claimed is:

1. A method of replacing a dispersion medium with another, comprising the steps of:
   feeding a starting slurry which comprises a first dispersion medium and isophthalic acid crystals to a cyclone-shaped nozzle disposed in an upper portion of a replacement tank of a dispersion medium replacement apparatus;
   contacting the starting slurry discharged from the cyclone-shaped nozzle with a second dispersion medium which is fed from a lower portion of the replacement tank and flows upwardly through the replacement tank; and
   mainly discharging a replaced slurry which comprises the isophthalic acid crystals and the second dispersion medium from the lower portion of the replacement tank and mainly withdrawing the first dispersion medium from the upper portion of the replacement tank, the cyclone-shaped nozzle comprising a hollow body of revolution having a vertically extending axis and an opening disposed at a vertically lower end, the starting slurry being tangentially fed to the hollow body of revolution so as to allow the starting slurry to move circularly along an inner wall of the hollow body of revolution, and the starting slurry which is circularly moving being discharged from the opening, thereby dispersing the starting slurry in the second dispersion medium.

2. The method according to claim 1, wherein an opening area of the opening is from 0.03 to 0.8 m$^2$.

3. The method according to claim 1, wherein the number of the cyclone-shaped nozzles per sectional area of the replacement tank is from 0.3 to 2/m$^2$.

4. The method according to claim 1, wherein the starting slurry is fed to two or more cyclone-shaped nozzles connected to a ring header.

5. The method according to claim 1, wherein the starting slurry is a reaction product solution of the liquid-phase oxidation of m-dialkylbenzene.

6. The method according to claim 1, wherein the starting slurry is a recrystallization slurry of crude isophthalic acid.

7. The method according to claim 1, wherein the starting slurry is discharged from the opening while keeping circular motion, such that the discharged slurry is dispersed in the horizontal direction by centrifugal force.

8. The method according to claim 1, wherein the hollow body of revolution has a weir at a lower portion thereof.

* * * * *